United States Patent [19]

Nashef

[11] Patent Number: 4,599,084
[45] Date of Patent: Jul. 8, 1986

[54] METHOD OF USING BIOLOGICAL TISSUE TO PROMOTE EVEN BONE GROWTH

[75] Inventor: Aws S. Nashef, Costa Mesa, Calif.

[73] Assignee: American Hospital Supply Corp., Evanston, Ill.

[21] Appl. No.: 497,624

[22] Filed: May 24, 1983

[51] Int. Cl.$^4$ .............................................. A61F 2/28
[52] U.S. Cl. ........................................ 623/16; 623/66
[58] Field of Search ................... 3/1 B, 1, 1.91, 1.911, 3/1.4, 1.5; 128/92 C

[56] References Cited

U.S. PATENT DOCUMENTS

| | | | |
|---|---|---|---|
| 4,218,782 | 8/1980 | Rygg | 3/1.5 |
| 4,323,358 | 4/1982 | Lentz et al. | 3/1.5 X |
| 4,400,833 | 8/1983 | Kurland | 3/1.91 X |
| 4,467,478 | 8/1984 | Jurgutis | 128/92 C X |

OTHER PUBLICATIONS

"Review of the Surgical Use of Implant Materials in Arthroplasty and a Potential Application of Porous Biomaterials to Recessional Arthroplasty" by W. H. Akeson, F. R. Convery, and D. W. Grainger in *Biomaterials–Bioengineering Applied to Materials for Hard and Soft Tissue Replacement* by Al Bement, Jr. (1971).
R. Dee, *Orthopedic Clinics of North America* 4 (2). 415–433 (1973).
N. Allison and B. Brooks in *Surgery, Gynecology and Obstetrics* (1913).

*Primary Examiner*—Richard J. Apley
*Assistant Examiner*—Alan W. Cannon
*Attorney, Agent, or Firm*—Donald L. Barbeau

[57] ABSTRACT

Disclosed is a method of using soft biological tissue to interface between a surgically implanted prosthesis, tendon or ligament, and the surface of resected bone to promote the even remodeling of said resected bone.

1 Claim, 11 Drawing Figures

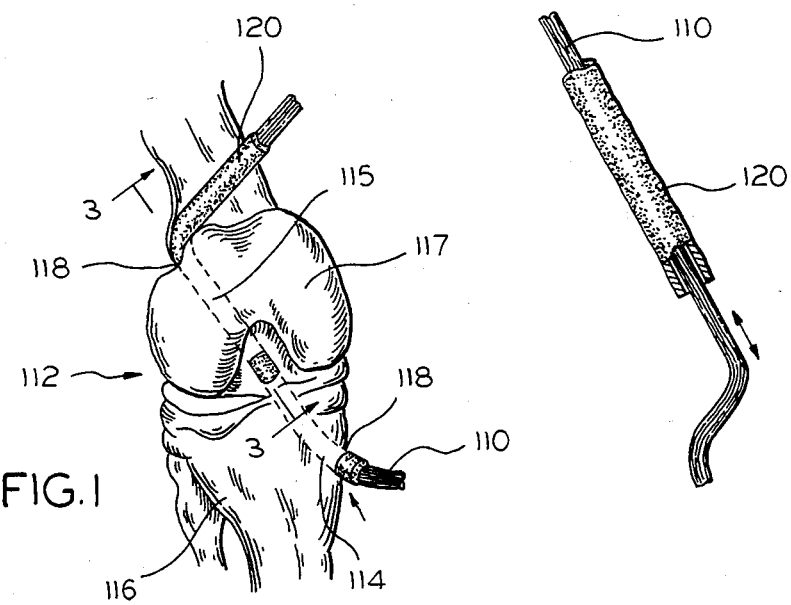
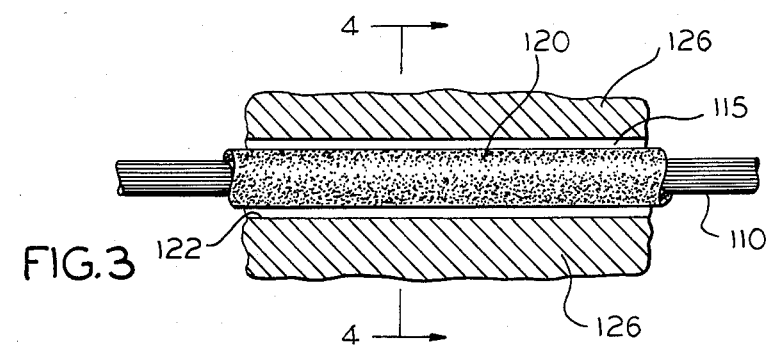
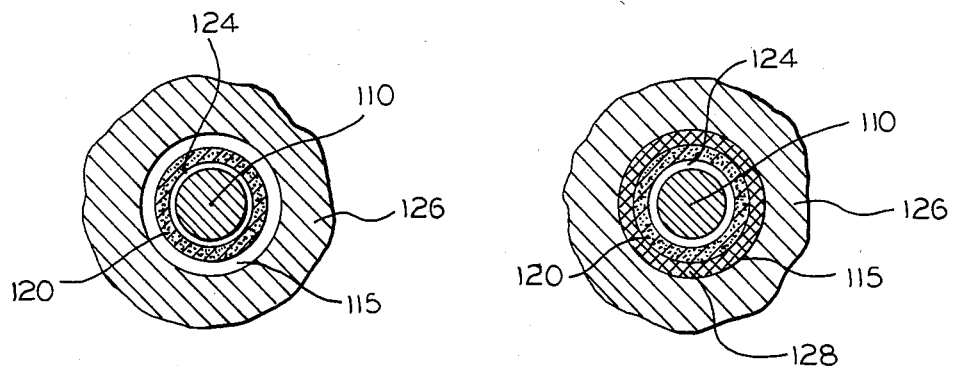
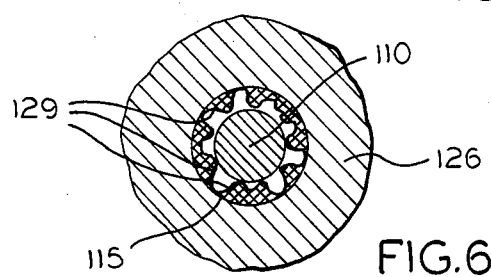

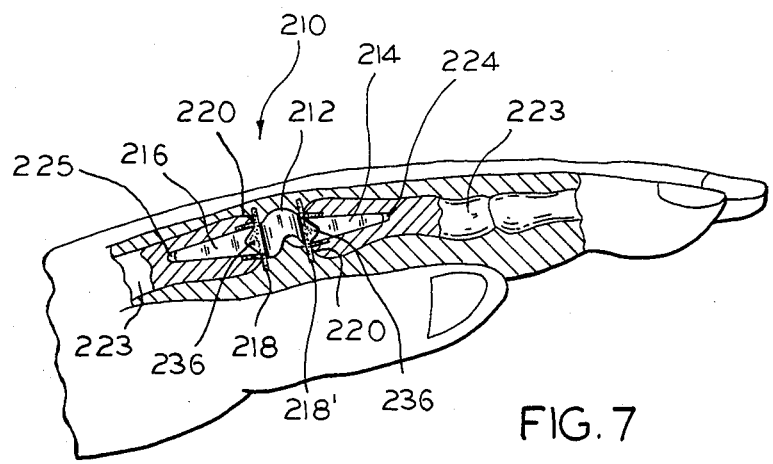
FIG. 7
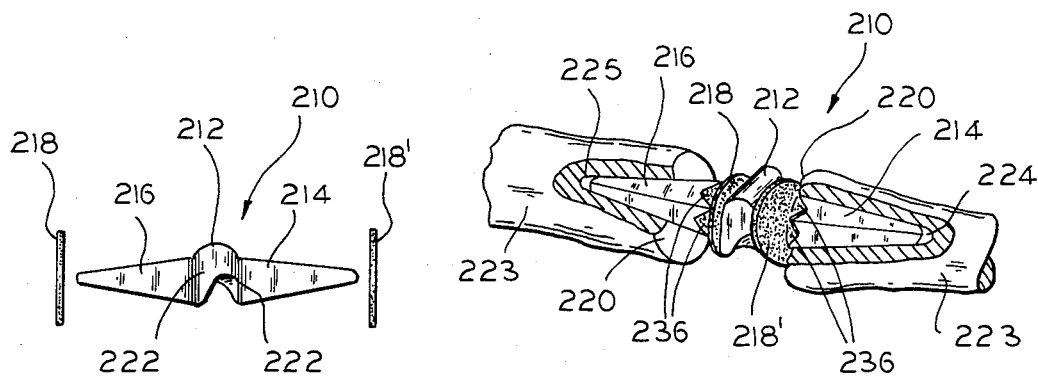
FIG. 8
FIG. 9
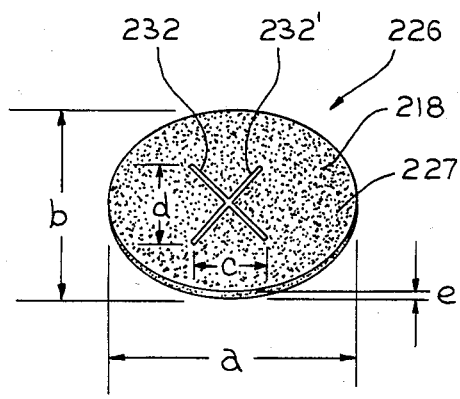
FIG. 10
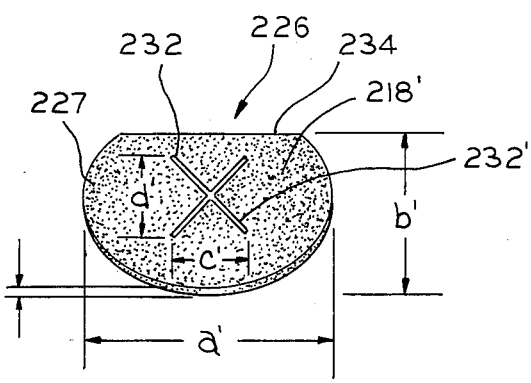
FIG. 11

METHOD OF USING BIOLOGICAL TISSUE TO PROMOTE EVEN BONE GROWTH

BACKGROUND OF THE INVENTION

Heretofore, surgically implantable prosthetic joints, together with tendon and ligament substitutes have been subjected to undesirable localized stress or lacerations and tearing caused by contact with sharp, irregular edges of bone growth on the surface of resected bone. This has often resulted in poor durability and performance of these implants. The present invention relates to a method of minimizing the deleterious effects of spurious bone growth adjacent surgically implanted prosthetic or biprosthetic implants.

Injury to weight-bearing ligaments such as the cruciate ligaments of the knee can occur, either as an isolated injury, or in combination with other ligament injuries of the knee. Damaged or torn cruciate ligaments can be repaired, reconstructed or treated nonoperatively depending upon the extent of the injury, the amount of functional or clinical laxity, the age of the patient, and the activity level desired. Simple repair of the injured ligament involves suturing, and because the cruciate ligaments are poorly vascularized, simple repair is generally insufficient. Reconstruction generally involves the utilization of synthetic ligament substitutes or autologous tissue within the knee joint similar to the cruciate ligament, such as in intraarticular reconstruction, or utilization of autologous tissue outside of the knee joint to strengthen the anterior or anterior lateral rotational stability, such as in extraarticular reconstruction.

Intraarticular reconstruction of anterior and posterior cruciate ligaments of the knee generally involves drilling holes through the tibia and femur followed by insertion of a ligament substitute such as patellar tendon, fascia, and the like through the central channel, and stapling of the ligament substitute to the outer surface of the bone adjacent the resected channel. The most common mode of failure is generally observed at the place where the ligament is subjected to stress; at the site where the ligament substitute enters or exits from the tibia or femur. Ordinarily the bone grows around and into the implanted ligament during the healing process leaving high stress concentrations at these exit sites. Moreover, the ingrowth of resected bone into the ligament implant throughout the length of the resected bone channel, which immobilizes the implant by restricting its naturally intended gliding motion and reducing its flexibility, may damage the implant due to sharp, jagged, irregular bone edges formed during the healing process.

Various attempts to improve the durability, compatibility, and mechanical functioning of naturally occurring and prosthetic tendons and ligaments have only been marginally successful. Such remedies include covering the ligament substitute with a vitreous carbon coating; plastic sheaths made of polyethylene, silicone rubber, and the like; silicone rubber-reinforced Dacron mesh sleeves; woven meshes of synthetic plastic fibers; stainless steel sleeves; metal wire meshes; and the like. Heretofore, implantable ligament substitutes in close proximity with resected bone have suffered the effects of irregular bone formation, high stress levels, and marginal durability.

Rheumatoid arthritis is an inflammatory disease of the soft tissues that causes severs destruction of the joint tissues. Inter alia, the disease weakens the capsule and ligament of the joint, causing the fingers to become displaced. Prior to the advent of implant arthroplasty of these joints, resection arthroplasty and a procedure known as fusion were the only alternatives to either relieve pain and to restore functional range of motion to the affected areas. Resection arthroplasty merely removed the joint capsule which allowed the space to fill in with a new surface of fibrous tissue, providing a false joint. Fusion caused a bond union across the joint, provided stability and relief of pain, but did not allow for motion in the fused joint. Implant resection arthroplasty is a surgical procedure performed to correct finger-joint deformation in patients with severe destruction of joints caused by progressive rheumatoid arthritis. A flexible elastomeric implant, preferably of silicone rubber, is the most commonly used adjunct to this arthroplasty procedure. Examples of such prosthetic joints include those disclosed in U.S. Pat. Nos.: 3,462,765; 3,593,342; 3,681,786; 3,818,513; 3,875,594; 3,879,767; 3,886,600; and 4,178,640.

One of the problems encoutered with these flexible implants is crack propogation and susceptibility to stress which ultimately leads to joint implant failure. During the healing processes following bone resection, sharp jagged edges of bone may develop which eventually initiate tears and cracks in the elastomeric implant. Swanson, in U.S. Pat. Nos. 4,158,893 and 4,198,713, has disclosed various protective devices for preventing lacerations or tearing of these flexible implants due to the damaging effects of the spur bone formation of the resected bone. In U.S. Pat. No. 4,158,893 the protective device is a sleeve adapted to fit within the intramedullary canal, wherein the sleeve is made of medical grade material such as porous polytetrafluoroethylene or high density polyethylene, which permits the bone to grow into its exterior surface. In U.S. Pat. No. 4,198,713, the protective device is a curvilinear shield adapted to conform to the upper portion of the prosthesis outer surface, wherein the shield is made of highly polished stainless steel which permits relative sliding, reciprocating motion between the prosthesis and the protective device.

In spite of the various improvements described hereinabove, the tearing and cracking of these prostheses has persisted. A need therefore exists for a device which interfaces between the flexible implants and the resected bone which not only discourages or inhibits the formation of bone spurs and sharp irregular bone, but promotes a smooth, regular, even remodeling of the resected bone surface and thus provides a smooth edge at this interface. Heretofore, no such device has been available.

SUMMARY OF THE INVENTION

In accordance with the present invention, disclosed is a method of interfacing a surgically implanted prosthetic or biological implant from contact with irregular bone edges of adjacent resected bone, comprising interposing a barrier layer of soft biological tissue at the interface of said resected bone and said implant, said layer of biological tissue having overall dimensions sufficient to cover at least a portion of the outer surface of said implant and a portion of said resected bone.

DESCRIPTION OF THE DRAWINGS

FIG. 1 is a front elevational view of a human knee having a cruciate ligament substitute implanted therein in accordance with one embodiment of the present invention;

FIG. 2 is an isolated view, partially cut away, of a ligament substitute sliding within the sleeve of one embodiment of the present invention;

FIG. 3 is a sectional view of the ligament and sleeve within the resected bone chanel of the femur, taken along line 3—3 of FIG. 1;

FIG. 4 is a cross-sectional view of the ligament and sleeve within the resected bone channel of the femur, taken along line 4—4 of FIG. 3;

FIG. 5 is a cross-sectional view similar to that of FIG. 4, showing the regular new bone growth between the surface of the resected bone channel and the sleeve of the present invention;

FIG. 6 is a cross-sectional view similar to that of FIGS. 4 and 5, showing the irregular new bone growth between the surface of the resected bone channel and the implanted ligament substitute without the benefit of the present invention.

FIG. 7 is a cross-section of the human hand showing the protective device in accordance with an alternate embodiment of the present invention;

FIG. 8 is an exploded front elevational view of a surgical implantable prosthesis used to replace bone joints and the protective device in one embodiment of the present invention;

FIG. 9 is an enlarged perspective view of the device shown in FIG. 1, having the bone partially sectioned to show the intramedullary canals;

FIG. 10 is a perspective view of the proximal protective device in accordance with one embodiment of the present invention;

FIG. 11 is a perspective view of the distal protective device in accordance with one embodiment of the present invention;

DETAILED DESCRIPTION OF THE PRESENT INVENTION

In accordance with a first embodiment of the present invention, disclosed is a substantially cylindrical sleeve for interfacing between surgically implantable tendon or ligaments and the interior surface of resected bone channels. By way of example, the sleeve may be inserted into the tibia and femur of a mammal for anterior and posterior cruciate ligament intraarticular reconstruction of the knee. The sleeve advantageously protects the implanted tendon or other suitable ligament substitute from damage caused by the growth of sharp, irregular edges on the resected bone surface; provides a moist environment of extracellular fluid around the implant and thus increases both its flexibility and durability; promotes relatively smooth remodeling or reshaping of the resected bone surface into a regular edge; and lowers stretching (stress levels) throughout the channel in the healing process since a larger portion of the full length of the implant may become available for shouldering strain, and consequently permits easier early motion of the knee after surgery.

For the purpose of illustrating the first embodiment of the present invention, a cruciate ligament substitute 110 implanted through the tibia and femur of the knee 112 is shown in FIG. 1. The ligament substitute is implanted in the knee 112 by drilling channels 114 and 115 through the tibia 116 and femur 117 respectively as shown in the drawing. The implant is shown having its truncated ends extending outwardly from the resected bone channel edge 118, however, it is to be understood that these ends are conventionally secured to the tibia 116 and femur 117 by stapling, and the like during the reconstructive surgery, which coes not constitute part of the present invention and will not be further described hereinafter.

In our illustration of intraarticular reconstruction, the cruciate ligament is normally replaced with autologous tissue such as fascialata, patellar tendon, semimembranous tendon, or synthetic ligaments such as polypropylene, proplast, Dacron, carbon fiber, polyethylene, and Teflon composites. In the broadest aspects of the present invention, the term implantable ligament substitute describes any synthetic or naturally occurring material which can be used to replace ligaments in the human body. These include, but are not limited to naturally occurring tendons and ligaments, biological tissue, or synthetic tendons and ligaments. Preferably, the ligament substitute will have from about 165 to about 390 pounds of tensile pull strength six months after surgery. The ligament substitute in accordance with one embodiment of the present invention is a glutaraldehyde-fixed bovine-bifurcated extensor tendon, and one which has preferably been treated prior to implantation with one of several available methods to reduce the calcification thereof after implantation. The sleeve of biological tissue in accordance with the present invention advantageously interfaces between resected bone and synthetic implants, which do not have the same properties as the fixed biological tissue of naturally occurring ligaments and tendons.

In accordance with the first embodiment of the present invention, a sheath or sleeve 120 is inserted into the resected bone channel 115 in order to interface between the resected bone surface 122 and the implanted ligament or tendon 110 such that a barrier is formed therebetween as shown in FIGS. 3 and 4. The external dimensions of the sleeve 120 will vary depending upon the length and cross-sectional area of the channel within the bone 126. In one embodiment of the present invention, the sleeve has a length sufficient to extend through at least a portion of the resected bone channel 115, and preferably is positioned at the external edge 118 of the channel. In an alternate embodiment of the present invention, the length of the sleeve 120 is sufficient to cover a major portion of the channel, and more preferably the entire interior surface of the resected bone channel is covered by the sleeve. In a preferred embodiment of the present invention, the sleeve has a length which is sufficient to cover the entire interior surface 122 of the resected bone channel and which is sufficient to extend beyond the edge 118 a short distance as shown by the arrow in FIG. 1. The portion of the sleeve 120 extending beyond this edge 118 is preferably flared outwardly. The cross-sectional area of the sleeve 120 is such that the outer surface of the sleeve will be in close proximity to the interior surface 122 of the resected channel, and preferably the outer surface of the sleeve has substantially the same diameter as that of the channel interior. The embodiment shown in the drawings shows a distance which is slightly exaggerated for ease of illustration. The sleeve 120 is preferably substantially cylindrical in shape so that it will conform to the interior of the channel, and resembles a tube having open ends and a longitudinal passage 124 extending therebetween. The internal dimensions of the sleeve are sufficient to receive a tendon or ligament substitute therethrough. By way of example, the preferred bovine-bifurcated extension tendon of the present invention is approximately 230 mm long, 8 mm wide, and 4 mm thick.

Alternately, the biological tissue may be relatively short and be shaped to fit into the ends of the resected channel 118 only and to extend outwardly around the entrance to the channel such that the ligament substitute will be covered by the tissue at the point it contacts the bone edge 118 and along the side of the bone adjacent the resected channel.

In accordance with the first embodiment of the present invention, the sleeve 120 is made of soft biological tissue such as naturally occurring biologial tissue derived from various animal sources including but not limited to bovine, porcine, horse, sheep, kangaroo, or rabbit; and can be obtained from various parts of the anatomy as described hereinbelow. Alternatively, the biological tissue can be composed of collagen or reconstituted collagen substitutes including but not limited to collagen-fabric films, collagen-membranes, reconstituted collagen on Dacron mesh, tanned collagen sponge grafts and the like. In accordance with the present invention, the soft biological tissue cushions the implant and provides a moist, lubricious, and flexible interface between the bone and implant; and also promotes the even, remodeling of resected bone resulting in a smooth bone surface. It is understood that soft biological tissue differs from hard biological tissue found in bone, teeth, and the like.

In accordance with a second embodiment of the present invention, disclosed is a protective device for surgically implantable prostheses used to repair resected bone or to replace bone joints. By way of example, the prosthesis may be of the type used for finger, toe, wrist, trapezium, carpal scaphoid, carpal lunate, and radial head implants, and may be a flexible elastomeric joint implant as described in U.S. Pat. Nos. 4,198,713; 4,158,893; 3,875,594; 3,462,765; 3,593,342; 3,681,786; 3,818,513; 3,879,767; 3,886,600; 4,178,640 which are hereby incorporated by reference into this application. Alternatively, the prosthesis may be of the type used in bone amputation, or any other bodily area where resected bone may grow in a jagged, irregular way, in the form of sharp edges that can cut the elastomeric surfaces of the prosthesis.

For the purpose of illustration, an implantable finger joint prosthesis is generally shown at 210 in FIGS. 7-9. The prosthesis is ordinarily made of flexible elastomeric material such as silicone rubber and sold under the trademark Silastic by Dow Corning Corporation, Midland, Mich. The prosthesis comprises a hinge-like flexible body portion 212 having a substantially rigid distal stem portion 214 directed outwardly from the body portion, and an outwardly-directed proximal stem portion 216 extending in a direction substantially opposite from that of the distal stem portion. It is to be understood that the stem portions 214 and 216 may project outwardly from the central body portion 212 at various angles depending on the exact configuration required to adapt the prosthesis to various implant sites.

The protective device 218 and 218′ in accordance with the second embodiment of the present invention is generally an oval web conforming to the major portion of the prosthesis body surface 212 that comes in contact with the resected bone surface 220 when fully implanted. As further described hereinbelow, the protective device is preferably constructed of fixed, soft biological tissue having overall dimensions sufficient to cover at least a portion of the outer surface 222 of the prosthesis body portion adjacent the stem portion 214, or 216 such that a prosthesis-to-bone interface is provided between at least a portion of the prosthesis when the prosthesis is inserted into the intramedullary canal.

In accordance with the second embodiment of the present invention, the protective device may be used in conjunction with any intermedullary stemmed flexible prosthetic implant where a resected bone-implant interface occurs. In paticular, these areas include wrist, toe, and the finger implants shown in FIG. 7. During a typical implantation procedure, the normal joint of a bone 223 is partially, surgically severed or resected leaving an exposed bone surface 220; and the intramedullary canals 224 and 225 are bored to receive the stem portions 214 and 216 of the prosthesis 210. After insertion of the implant, sharp, jagged edges of bone normally develop particularly at the resected bone surface 220 which eventually initiate a crack in the flexible implant. In accordance with one embodiment of the present invention, the protective device 218 and 218′ is interposed between the exposed resected bone surface and the prosthetic implant 210 and acts as a barrier or interface therebetween to promote relatively smooth remodeling or reshaping of the bone surface into a regular edge and shield the implant from sharp bone spurs.

In accordance with the present invention, the protective device 218 and 218′ is generally disc-shaped as generally shown at 226 in FIGS. 10 and 11. In accordance with one embodiment of the present invention, the external dimensions of the said tissue are sufficient to cover substantially the entire outer surface 222 of the prosthesis body portion 212 adjacent the stem portion such that a prosthesis-to-bone interface is provided between substantially all of the resected bone surface 220 and the body portion 222 of the prosthesis when the implant is inserted into the intramedullary canal 224 and 225. Thus, it will be understood that the external dimensions of the tissue 226 will be dependent upon the size of the prosthesis which, in turn, is dependent upon the type of joint replacement and site at which the joint is replaced.

A web in accordance with one embodiment of the present invention, is a piece of shaped biological tissue having generally planar faces 227 defining an area which has lateral dimensions relatively larger than the thickness of the tissue.

In a preferred embodiment of the present invention, the external dimensions of said tissue are sufficient to cover at least a portion of the stem portion adjacent the prosthetic body portion in addition to covering the body portion as described above such that a prosthesis-to-bone interface is additionaly provided between a portion of the exposed resected bone in the intramedullary canal and a portion of the stem portion.

In a preferred embodiment of the present invention, the protective device is of biological tissue cut in a generally oval shape as shown in FIGS. 10 and 11. The proximal tissue 218 depicted in FIG. 10 has a major axis (a) of from about 0.32 to about 0.73 inches, and a minor axis (b) of from about 0.16 to about 0.53 inches. The tissue, which is approximately 0.016 inches in depth (e), has a pair of intersecting slits 232 and 232′ cut through its face 227 for providing an aperture for passage of the prosthesis stem portion. The intersecting slits are generally X-shaped, and describe an area from end-to-end having lateral dimensions (c) of from about 0.10 to about 0.29 inches and (d) of from about 0.10 to about 0.29 inches.

The distal tissue 218' depicted in FIG. 11 is generally similar to the proximal web 218; however, it has a truncated side portion 234. The tissue has a major axis (a') of from 0.32 to about 0.73 inches, a minor axis (b') of from 0.15 to about 0.52 inches, and intersecting slits 232 and 232' describing an area from end-to-end having lateral dimensions of (c') from about 0.10 to about 0.29 inches, and (d') from about 0.08 to about 0.25 inches, and a thickness (e') of approximately 0.016 inches.

In accordance with the present invention, the biological tissue is either naturally occurring biological tissue derived from various animal sources including but not limited to bovine, porcine, horse, sheep, kangaroo, or rabbit; and can be obtained from various parts of the anatomy as described hereinbelow. Alternatively, the biological tissue can be composed of collagen or reconstituted collagen substitutes including but not limited to collagen-fabric films, collagen-membranes, reconstituted collagen on Dacron mesh, tanned collage sponge grafts and the like. In accordance with the present invention, the soft biological tissue provides a moist lubricious, flexible interface between the bone and implant; and also promotes the even, remodeling of resected bone resulting in a smooth bone surface. Moreover, the biological tissue is stable when implanted into the body. It is well understood that soft biological tissue differs from hard biological tissue found in bone, teeth, and the like.

In accordance with the present invention, naturally occurring biological tissue is removed from its host, defatted if necessary and processed in one of several well-known procedures used to prepare the tissue for implantation into humans. The tissue is fixed (tanned) conventionally in from about 0.2 to about 0.6 weight percent glutaraldehyde in either phosphate-buffered solutions, or phosphate-free buffers as described in the copending U.S. patent application Ser. No. 445,345 filed on Nov. 29, 1982. The tissue handling conditions, as conventionally known, are not considered part of the present invention unless otherwise stated. Likewise, tissue may be sterilized conventionally in about 0.625 percent glutaraldehyde or from about 4 to about 5 percent formaldehyde.

Naturally occuring biological tissue in accordance with the present invention includes, but is not limited to epithelial and fibrous connective tissue such as pericardial tissue, dura mater, fascialata, amnion, tendon, ligament, cartilage, and the like. Veins and arteries already shaped in a sleeve-like structure are also useful in the present invention. The epithelial tissues such as dura mater, amnion, facialata, and percardium generally comprise two layers each; a fibrous, proteinaceous layer and a relatively smooth membranous layer. In accordance with a preferred embodiment of the present invention, the rough, fibrous layer of the tissue is placed against the resected bone to provide better anchoring to the bone surface, while the smooth, membranous layer is directed toward the surgical implant and provides a more lubricious surface. In accordance with the first embodiment of the present invention, pericardial tissue which has its edges sewn together to form an elongated tube-like structure is the preferred sleeve.

In accordance with the most preferred embodiment of the present invention, the natural biological tissue is treated prior to implantation to render it substantially resistant to calcification. This advantageously maintains the biological tissue in a more flexible state than calcified tissue, allowing the tissue to conform better to the uneven surface of the resected bone, and provides a softer surface to the resected bone prompting better bone healing. For example, in the first embodiment of the present invention the calcification-resistant sleeve will ultimately reduce the calcium deposits in the interior passage 24 of the sleeve 20 where the ligament substitute must be able to move freely as shown in FIG. 2. Calcification mitigation treatments of biological tissue are not considered part of the present invention but can be found in copending U.S. patent applications Ser. Nos. 445,345 filed Nov. 29, 1982; and Ser. No. 441,023 filed Nov. 12, 1982; and in U.S. Pat. No. 4,323,358 and U.S. Pat. No. 4,481,009.

In accordance with one embodiment of the present invention, we have found significant differences in the formation of new surfaces on resected bone when using sleeves of glutaraldehyde-fixed biological tissue inserted into the drilled holes of the tibia and femur than when no such sleeves are used. First, we drilled holes having a diameter of 0.172 inches in the tibia and femur of a rabbit adjacent the knee and observed that the resected bone randomly grew throughout the interior of the resected channel. Secondly, and in a separately drilled hole, we inserted a glutaraldehyde-fixed tendon through the tibia and femur of a rabbit knee and observed that the resected bone grew around the periphery of the channel in a somewhat irregular pattern as illustrated in FIG. 6 at 29. We repeated this experiment, but this time used a glutaraldehyde-fixed tendon which had been treated prior to implantation to render the tendon substantially resistant to calcification. We observed similarly-formed irregular bone growth about the periphery of the channel; however, the tendon did not calcify within passageway 24 and was not visible by X-rays. Finally, we formed a sleeve of glutaraldehyde-fixed pericardial tissue by sewing the tissue into a tube-like structure, having an external diameter substantially the same as the bone channel interior with the fibrous layer on the exterior surface, and inserted this sleeve into the bone channel. Substantially uniform bone growth around the periphery of the channel was observed, resulting in a substantially cylindrical channel free of jagged bone edges within the resected bone as illustrated at 28 in FIG. 5. The sleeve of biological tissue not only contained the bone growth between the exterior of the sleeve and the interior surface of the resected bone channel, but more importantly it promoted the smooth, even, remodeling of the bone 28 at this interface.

In accordance with the second embodiment of the present invention, the protective device 218 and 218' is intended to minimize the potential for prosthetic implant fracture by acting as a spacer between the joint implant 210 and the resected bone surface 220. Studies conducted in rabbits, as described hereinafter, show that when the protective device 218 and 218' is placed in contact with resected bone, the bone healing process results in a smooth bone surface with minimal inflammation and no necrosis.

Animal Studies

The rabbit knee was used as the experimental model because the size of the rabbit's knee joint is comparable in size to that of the human finger joint. The animal study consisted of two groups. The control group animals received the prosthetic implant without the protective device, and the experimental group received the prosthetic implant with the protective device. After six and twelve weeks, the implants were retrieved from the rabbits and examined for wear and cellular activity. Histology was performed on the bone protective device interface and on the capsule surrounding the joint space to determine host cellular reaction to the protective device and the implant.

The histological evaluation of 36 silicone joint implants retrieved from 36 rabbits indicates that the presence of biological tissue interposed between the implant and resected bone surface in accordance with the present invention significantly reduced wear of the silicone implant, indicating that the implant will function longer without fracturing when implanted into humans.

The silicone joint implant showed pathological evidence of wear debris as is common in many prosthetic materials. The amount of silicone debris was not only related to the length of time the implant was in place, but more importantly to stress factors. The most important factors appeared to be related to sharp bone edges at the ostial opening and to fibro-osseous "humps" which formed in the surgical channel in which the prosthesis was placed. Abrasions and gouges were most prominent on the tibial side of the implant, particularly in the control animals. The silicone debris resulted in predominantly a mononuclear histiocyte response and a mild to moderate multinucleate histiocyte response, generally mild to moderate chronic inflammation and eventually fibrosis, most always in direct proportion to the amount of debris. The control animals showed significantly great amounts of silicone debris than did the experimental animals; which would be expected when the device minimizes wear.

The biological tissue, when it covered the ostial surface, the entrance edge of bone, and the upper channel into the bone significantly reduced silicone wear. The tissue caused little histiocytic reaction or chronic inflammation. There was no acute inflammation or necrosis caused by either the tissue or the silicone debris in any experimental time period even as early as two weeks. In one case, the tissue was being bound down on its lateral deep edges by living rabbit fibroblasts and incorporated as Sharpey's-like fibers into rabbit cartilage with no adverse tissue reaction.

The following table shows the comparison of the implants in the control animals with those using biological tissue as a protective device.

TABLE 1

| Observation | % of animals | |
|---|---|---|
| | Control (n = 7) | With Biological Tissue (n = 10) |
| Moderate wear and cracking to completely fractured implant and/or deformation (implant failure) | 43% | 10% |
| Slight wear, scratching and/or deformation (normal wear) | 43% | 20% |
| Minimal or no signs of wear, no distinct lacerations of the implant surface (normal wear) | 14% | 70% |

TABLE 1-continued

| Observation | % of animals | |
|---|---|---|
| | Control (n = 7) | With Biological Tissue (n = 10) |

The protective device 218 and 218', in accordance with the present invention, can be placed around the stem portion 214 and 216 of a surgically implantable prosthesis 10 and sold in a fully assembled manner, or they may be packaged in a sterile sealed package (jar) separately from a prosthesis such that the physician or surgeon can place the device on the prosthesis just prior to implantation. Preferably, and by way of example, a distal 218' and proximal 218 device may be contained in a sterile package. Prior to insertion of the implant into the intramedullary canal 224 and 223 of the resected joint bone, the webs are placed on the stems 214 and 216 of the implant with the smooth side of the tissue facing the body portion of the prosthesis. The fibrous, textured side is directed away from the prosthesis and toward the surface of the resected bone. The distal web is placed on the distal stem of the prosthesis with the truncated 234 edge facing toward the palmar surface. Preferably the web has a pair of slits 232 and 232' in its face 227 that form flaps 236 to cover a portion of the stem adjacent the body of the prosthesis. These flaps 236 preferably fit snugly and squarely around the stem of the prosthesis. Once the proximal stem of the prosthesis is in the intramedullary canal of the metacarpal, the implant is flexed so that the distal stem can easily be inserted into the proximal phalanx with the flaps carefully tucked into the bone canal. With the joint in extension, there should be no impingement of the implant; and the webs should preferably be flat against the midsection of the implant and not restrict its movement or function.

The present invention has been described in detail and with specific reference to its preferred embodiments, however, it will be understood by those skilled in the art that modifications can be made thereto without departing from the spirit and scope thereof.

I claim:

1. A method of interfacing a surgically implanted prosthetic or biological implant from contact with the surface of resected bone comprising interposing a barrier layer of glutaraldehyde-fixed pericardial tissue at the interface of said resected bone and said implant, such that the fibrous surface of the fixed pericardial tissue is disposed in direct contact with the resected bone to allow for bone tissue ingrowth into said fibrous surface; said tissue being further treated such that it is substantially resistant to calcification; and said layer of pericardial tissue having overall dimensions sufficient to cover at least a portion of the outer surface of said implant and a portion of said resected bone.

* * * * *